United States Patent [19]

Albers-Schonberg et al.

[11] 4,342,767
[45] Aug. 3, 1982

[54] HYPOCHOLESTEREMIC FERMENTATION PRODUCTS

[75] Inventors: George Albers-Schonberg, Princeton; Richard L. Monaghan, Somerset; Alfred W. Alberts, Short Hills; Carl H. Hoffman, Scotch Plains, all of N.J.

[73] Assignee: Merck & Co., Inc., Rahway, N.J.

[21] Appl. No.: 159,983

[22] Filed: Jun. 16, 1980

Related U.S. Application Data

[63] Continuation-in-part of Ser. No. 114,459, Jan. 23, 1980, abandoned, which is a continuation-in-part of Ser. No. 48,946, Jun. 15, 1979, Pat. No. 4,231,938.

[51] Int. Cl.³ .................. A61K 31/22; C07C 69/74
[52] U.S. Cl. ......................... 424/250; 424/273 B; 424/289; 260/429.9; 260/448 R; 544/358; 548/327; 560/119; 560/252; 560/256; 435/125; 435/135; 435/913; 549/292
[58] Field of Search .............. 560/119, 252, 256; 548/327; 544/358; 424/305, 311, 289, 273 B, 250; 260/429.9, 448 R

[56] References Cited

U.S. PATENT DOCUMENTS 4,020,094  4/1977  Nelson et al. .................. 260/501.11
4,137,322  1/1979  Endo et al. .................... 560/119

OTHER PUBLICATIONS

A. Endo et al., FEBS Letters, vol. 72, No. 2, (1976), pp. 323–326.
A. Endo et al., Eur. J. Biochem., vol. 77, (1977), pp. 31–36.

Primary Examiner—Natalie Trousof
Assistant Examiner—Frederick W. Pepper

Attorney, Agent, or Firm—William H. Nicholson; Mario A. Monaco

[57] ABSTRACT

Substances isolated after cultivation of a microorganism belonging to the genus Aspergillus in a culture medium comprise compounds which have structures:

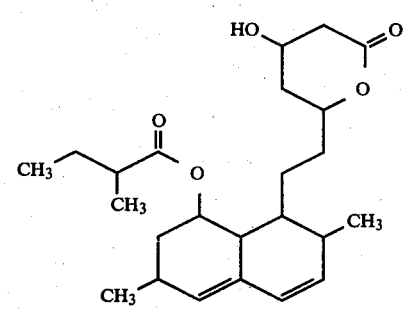

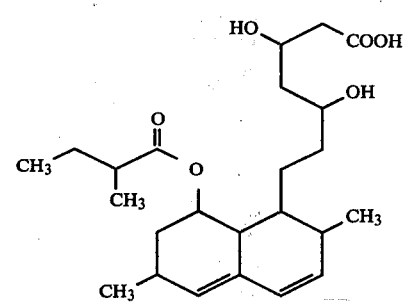

Together with salts and esters of the carboxylic acid, these compounds form a class of highly active hypocholesteremic and hypolipemic medicaments.

12 Claims, 2 Drawing Figures

Fig. 1.

Fig. 2.

HYPOCHOLESTEREMIC FERMENTATION PRODUCTS

This is a continuation-in-part of copending application Ser. No. 114,459, filed Jan. 23, 1980, now abandoned, which in turn is a continuation-in-part of application Ser. No. 048,946, filed June 15, 1979, now U.S. Pat. No. 4,231,938.

SUMMARY OF THE INVENTION

This invention relates to hypocholesteremic products from the cultivation of a microfungus of the genus Aspergillus. More specifically, it relates to compounds of the formulae:

as well as pharmaceutically acceptable salts and lower alkyl and substituted alkyl esters of the carboxylic acids in which the possible substituent is phenyl, dimethylamino or acetylamino. The invention also relates to a process of cultivating the microfungus and isolating from the medium a hypocholesteremic compound of the above structures. These new compounds have excellent properties of inhibiting cholesterol biosynthesis and are useful against hypercholesteremia and hyperlipemia.

BACKGROUND OF THE INVENTION

Because of the possible connection between high blood cholesterol and atherosclerosis, many efforts have been made to find ways and substances which would reduce the cholesterol in the mammalian body. One of these ways is to inhibit in mammals the body's ability to synthesize cholesterol.

Recently, Endo et al., described (U.S. Pat. Nos. 4,049,495 and 3,983,140) a fermentation product obtained by cultivation of a microorganism of the genus Penicillium and isolation from the medium. They called it ML 236 B and determined its structure together with two related compounds 236 A and 236 C. Its structure, under the name compactin, was also determined by A. G. Brown, T. C. Smale, T. J. King, *J. Chem. Soc.* (Perkin I) 1165 (1975). This compound has been found to be an inhibitor, in vivo, of the biosynthesis of cholesterol.

DESCRIPTION OF THE INVENTION

We have found that unexpectedly, the cultivation of a microorganism very different from that employed by Endo, a microfungus of the genus Aspergillus, produces new substances that are also very potent inhibitors of the biosynthesis of cholesterol in mammals. We have further found that these substances comprise principally the new compounds I and II, of the above structures, accompanied by only traces of other compounds. These new compounds are much more potent inhibitors of cholesterol synthesis in vivo than is the compound, ML236B described by Endo.

The pharmaceutically acceptable salts of this invention include those formed from cations such as sodium, potassium, aluminum, calcium, lithium, magnesium, zinc, ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, tris(hydroxymethyl)aminomethane, and tetramethylammonium.

The compounds of this invention are highly useful as antihypercholesteremic agents for the treatment of atherosclerosis, hyperlipemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg. to 2000 mg. (preferably 2 to 100 mg) which may be given in two to four divided doses. Higher doses may be favorably employed as required.

The compounds of this invention also have useful antifungal activities. For example, they may be used to control strains of *Penicillium sp.*, *Aspergillus niger*, *Cladosporium sp.*, *Cochliobolus miyabeanus* and *Helminthosporium cynodnotis*. For those utilities they are admixed with suitable formulating agents, powders, emulsifying agents or solvents such as aqueous ethanol and sprayed or dusted on the plants to be protected.

In another aspect of this invention, it relates to a process for producing the compounds of this invention which comprises cultivating a microorganism belonging to the genus Aspergillus and then recovering said compounds of this invention from the cultured broth. Based upon taxonomic studies, this Aspergillus, isolated and identified as a hitherto undescribed microorganism, has been designated MF-4833 in the culture collection of Merck and Co., Inc., Rahway, N.J. and a culture thereof has been placed on permanent deposit with the American Type Culture Collection, 12301 Parklawn Drive, Rockville, Md. 20852, and has been assigned accession number ATCC 20541. Another sample, of a similar organism, designated MF-4845 in the Merck culture collection, has likewise been placed on deposit and has been given the accession number ATCC 20542. The latter organism is the one giving the better yield. Although the use of these is described in connection with the process of this invention, other organisms of the genus Aspergillus including mutants of the above ones are also capable of producing these novel compounds and their use is contemplated in carrying out the process of this invention.

The morphological characteristics of the microorganisms MF-4833 and MF-4845 have been found to be those of the genus Aspergillus. Using the criteria specified in the standard authority "Manual of the Aspergilli", Charles Thom and Kenneth B. Rasper, published by the Williams and Wilkins Company, Baltimore, Md., 1945, and by comparison with known species, it has been determined that both strains are *Aspergillus terreus*.

The culture of these organisms to produce the novel compounds is carried out in aqueous media such as those employed for the production of other fermentation products. Such media contain sources of carbon, nitrogen and inorganic salts assimilable by the microorganism.

In general, carbohydrates such as sugars, for example, glucose, fructose, maltose, sucrose, xylose, mannitol and the like and starches such as grains, for example, oats, ryes, cornstarch, corn meal and the like can be used either alone or in combination as sources of assimilable carbon in the nutrient medium. The exact quantity of the carbohydrate source or sources utilized in the medium depend in part upon the other ingredients of the medium but, in general, the amount of carbohydrate usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include for example, yeast hydrolysates, primary yeast, soybean meal, cottonseed flour, hydrolysates of casein, corn steep liquor, distiller's solubles or tomato paste and the like. The sources of nitrogen either alone or in combination, are used in amounts ranging from about 0.2% to 6% by weight of the aqueous medium.

Among the nutrient inorganic salts which can be incorporated in the culture media are the customary salts capable of yielding sodium, potassium, ammonium, calcium, phosphate, sulfate, chloride, carbonate, and like ions. Also included are trace metals such as cobalt, manganese, iron and magnesium.

It should be noted that the media described in the Examples are merely illustrative of the wide variety of media which may be employed, and are not intended to be limitative. Specifically, the carbon sources used in the culture media to produce the novel compounds of this invention included dextrose, dextrin, oat flour, oatmeal, molasses, citrate, soybean, oil, glycerol, malt extract, cod liver oil, starch, ethanol, figs, sodium ascorbate and lard oil. Included as nitrogen sources were peptonized milk, autolyzed yeast, yeast RNA, tomato paste, casein, primary yeast, peanut meal, distillers solubles, corn steep liquor, soybean meal, corn meal, NZ amine, beef extract, asparagine, cottonseed meal and ammonium sulfate. The major ionic components were $CaCO_3$, $KH_2PO_4$, $MgSO_4.7H_2O$ and NaCl and small amounts of $COCl_2.6H_2O$ and traces of Fe, Mn, Mo, B and Cu were also present.

The fermentation is carried out at temperatures ranging from about 20° to 37° C.; however, for optimum results it is preferable to conduct the fermentation at temperatures of from about 22° to 30° C. The pH of the nutrient media suitable for growing the Aspergillus culture and producing the novel compounds can vary from about 6.0 to 8.0.

Although the novel compounds are produced by both surface and submerged culture, it is preferred to carry out the fermentation in the submerged state. A small scale fermentation is conveniently carried out by inoculating a suitable nutrient medium with the Aspergillus culture and, after transfer to a production medium, permitting the fermentation to proceed at a constant temperature of about 28° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 28° C. for 2 days, or until growth is satisfactory, and some of the resulting growth is used to inoculate either a second stage seed or the production medium. Intermediate stage seed flasks, when used, are developed in essentially the same manner, that is, part of the contents of the flask from the last seed stage are used to inoculate the production medium. The inoculated flasks are shaken at a constant temperature for several days, and at the end of the incubation period the contents of the flasks are centrifuged or filtered.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of time as, for example, from 3 to 5 days while agitating and/or aerating the nutrient medium and maintaining the temperature at about 28° C. This method of producing the novel compounds is particularly suited for the preparation of large quantities.

The compounds are conveniently isolated from the fermentation broth as the lactone (I), or as salts of Compound II.

Compound I can be hydrolyzed with bases such as NaOH to yield the salts such as the sodium salt of Compound II. The use of bases with other pharmaceutically acceptable cations affords salts of these cations. Careful acidification of the salts affords the hydroxy acid II. The hydroxy acid II can be converted to Compound I at acidic pH. Treating Compound I under acidic or basic catalysis with methanol, ethanol, propanol, or butanol or with phenyl, dimethylamino, or acetylamino alkanols yields the corresponding esters of Compound II which also form a part of this invention.

Compound II can be conveniently isolated without need of chromatography, in the form of the ammonium salt. The process comprises acidifying whole broth, preferably with phosphoric acid and preferably to about pH 5; extracting the acidified broth with a water-immiscible, inert, organic solvent, preferably ethyl acetate; extracting the organic solvent extract with aqueous alkali, such as 0.1 to 0.5 N sodium hydroxide; reacidification to pH 5 with phorphoric acid; extracting the acidified aqueous extract with a water-immiscible, inert, organic solvent preferably a mixture of n-hexane/ethyl acetate and preferably about a 2:1 (v/v) mixture; drying the extract; and bubbling in gaseous ammonia causing precipitation of the ammonium salt. This isolation is convenient and is much more adapted to commercial use than is chromatography. Furthermore, salts of II are much more active than compound I in vitro in the inhibition of cholesterol biosynthesis and as antifungal agents. Therefore, these salts are one of the especially preferred dosage forms. Preferred salts, in addition to ammonium, include tetramethylammonium, and salts of ethylenediamine, sodium, potassium, calcium, N-methylglucamine, lysine, arginine and ornithine.

The physico-chemical properties of compound I (MSD-803) are summarized as follows:

| 1. | Melting point | 170–171° |
|---|---|---|
| 2. | Molecular Weight (mass spectrum) | 404 |
| 3. | Formula (found by mass spectrometry calculated) | $C_{24}H_{36}O_5$ 404.2555 404.2563 |
| 4. | UV Spectrum (in acetonitrile): | Maxima 230.5 nm with E % 505.7 237.5 nm with E % 576.6 246 nm with E % 395.2 |

5. $^{13}C$ NMR chemical shifts

The spectrum has been recorded in $CDCl_3$ solution (20.1 mg in 0.35 ml). Chemical shifts are given relative to internal tetramethylsilane at zero ppm; under the experimental conditions the solvent ($CDCl_3$) signal appears centered at 70.0 ppm. In agreement with mass spectral data 24 carbon atoms are observed; their chemical shifts are: 11.5, 13.6, 16.0, 22.6, 24.1, 26.6, 27.2, 30.5, 32.5, 32.8, 35.9, 36.4, 37.1, 38.4, 41.3, 62.4, 67.8, 76.4, 128.4, 129.7, 131.7, 133.2, 170.8 and 177.2 ppm.

6. $^1H$ NMR Spectrum

Figure 1:
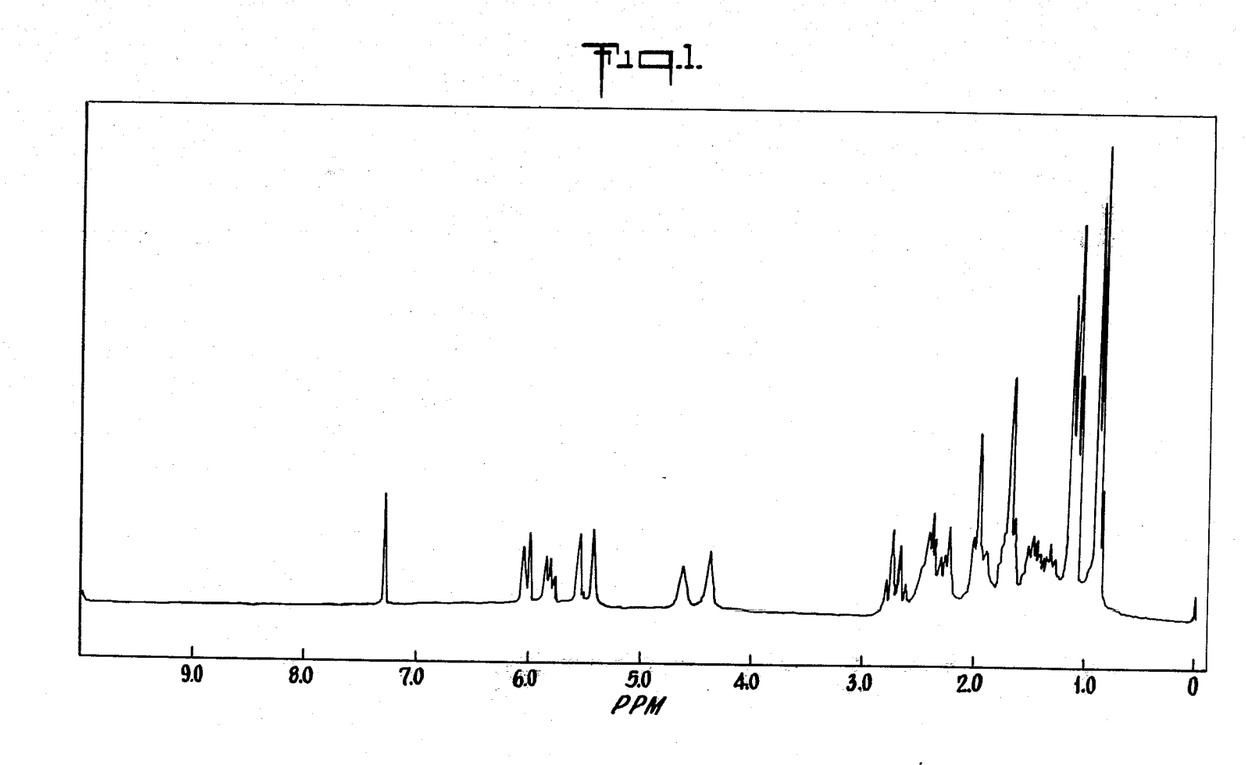

The spectrum was recorded in $CDCl_3$ solution and chemical shifts are shown in FIG. 1 in ppm relative to internal tetramethylsilane at zero ppm.

7. IR Spectrum

Figure 2:
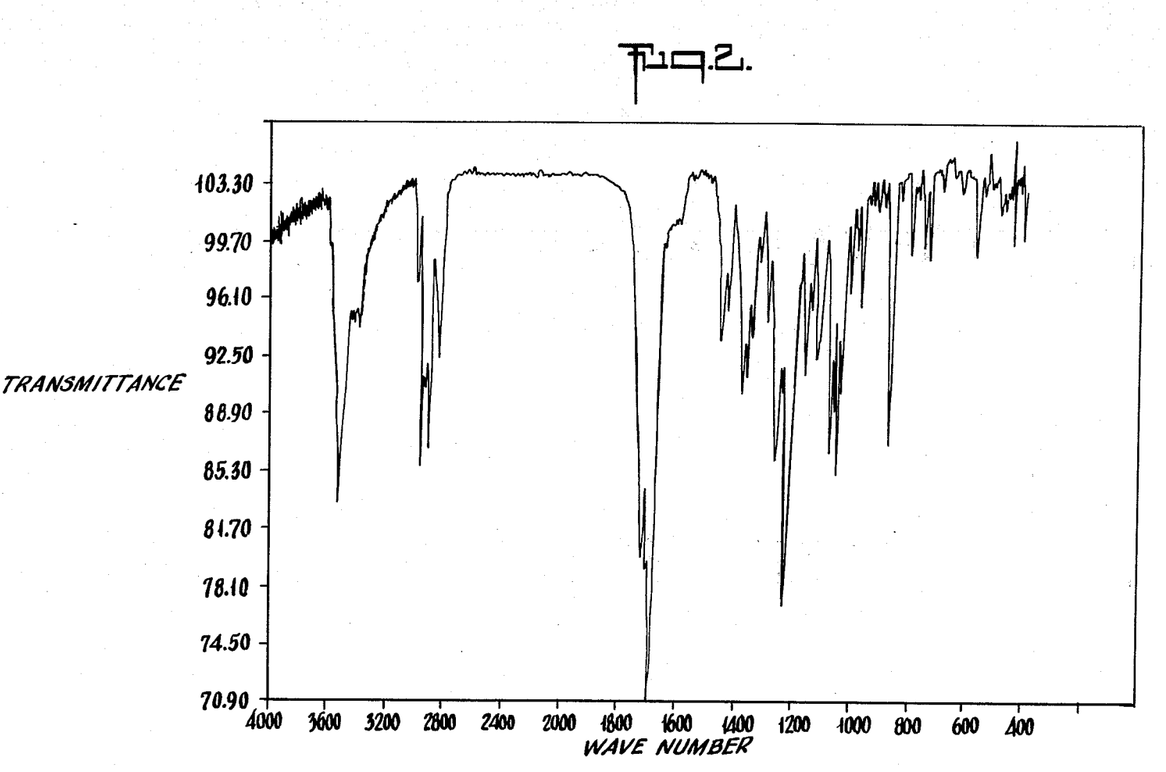

The infra red spectrum was recorded in a KBr pellet preparation of a sample. It is shown in FIG. 2.

8. Optical rotation.

The specific optical rotation $[\alpha]_D^{25} = 320.7°$ has been determined on a solution of 5.30 mg/ml $CH_3CN$.

This value has been obtained by measuring at the sodium-D-line wave length. On the basis of these and other data, the structure of the product is believed, with a considerable degree of certainty, to have the stereo chemical structure:

The corresponding hydroxy acid compound II, has the structure:

The absolute configuration of the centers of assymetry in these molecules has been determined from X-ray diffraction patterns.

This invention can be illustrated by the following examples.

EXAMPLE 1

Preparation of Compounds I and II

A. Fermentation

A tube of lyophilized culture MF-4833 is opened aseptically and the contents suspended in an unbaffled 250 ml Erlenmeyer flask (seed flask) containing approximately 20 ml of medium A. Medium A has the following composition:

| Medium A | |
|---|---|
| Corn steep liquor | 10 g |
| Tomato paste | 80 g |
| Oatmeal | 20 g |
| Glucose | 20 g |
| Trace Element Mix No. 2 | 20 ml |
| Distilled water | 1000 ml |
| pH 6.8 with NaOH | |
| Trace Element Mix No. 2 | |
| $FeSO_4.7H_2O$ | 1000 mg |
| $MnSO_4.4H_2O$ | 1000 mg |
| $CuCl_2.2H_2O$ | 25 mg |
| $CaCl_2.2H_2O$ | 100 mg |
| $H_3BO_3$ | 56 mg |
| $(NH_4)_6Mo_7O_{24}.4H_2O$ | 19 mg |
| $ZnSO_4.7H_2O$ | 200 mg |
| Distilled Deionized Water | 1000 ml |

The inoculated flask is incubated for 48 hours at 28° C. on a 220 rpm shaker (2 inch throw). Two unbaffled 2 liter Erlenmeyer flasks each containing 500 ml of medium B are then each inoculated with 10 ml per flask of the growth from the seed flask. Medium B has the following composition:

| Medium B | |
|---|---|
| Tomato paste | 20 g |
| Primary yeast | 10 g |
| CPC Starch | 20 g |
| $CoCl_2.6H_2O$ | 5 mg |
| Distilled water | 1000 ml |
| pH 7.2–7.4 with NaOH | |

These two inoculated flasks are incubated for 96 hours at 28°. One flask is incubated without agitation. The other flask is incubated on a 150 rpm shaker (2" throw). After 96 hours, the contents of each flask is set aside for isolation of the product.

B. Isolation of Compound I

The whole broth is centrifuged for 20–30 min. Solids are saved for extraction. The supernatant liquid (pH 6-8) is charged to a 950 ml bottle and 150 ml XAD-2 resin is added. Using an automatic Extractor, operating on a preset schedule, the mixture is stirred for 2 hours. The spent broth is then siphoned off and discarded. The resin is washed twice with 200 ml of deionized water and the washes were discarded. There then is added a charge of 300 ml of mixed solvent: isopropanol-ethyl acetate-dichloromethane 25-45-30. The mixture is stirred two hours. The solvent-resin slurry is filtered on a Buchner or sintered glass funnel and the resin is discarded. The broth solids are stirred with 100 ml acetone for ½ hour. The mixture is then centrifuged and the supernatant liquor is decanted. The combined filtrate and decantate are concentrated to 15 ml.

C. Testing of Compound I

The filtrates were tested as inhibitors of HMG-CoA reductase enzyme by the method described by Beg, Stonik, and Brewer (1977 *FEBS Letters* 80 123 to 129) using enzymes prepared as described by Kleinsek, Rangatham and Porter (1977 *Proc. Nat. Acad. Sci.* 74 1431 to 1435). The positive test (over 90% inhibition at 20 micrograms per milliliter—an $IC_{50}$ of 2.3 micrograms per milliliter indicated the presence of a very potent inhibitor of sterol synthesis acting at the HMG-CoA reductase level.

EXAMPLE 2

Preparation of Compounds I and II

A. Fermentation

A tube of lyophilized culture of an Aspergillus sp. MF-4833 is opened aseptically and the contents suspended in an unbaffled 250 ml Erlenmeyer flask (seed flask No. 1) containing 40 ml of medium C. Medium C has the following compositions:

| Medium C | |
|---|---|
| Corn steep liquor | 5 g |
| Tomato paste | 40 g |
| Oatmeal | 10 g |
| Glucose | 10 g |
| Trace element | |
| Mix No. 2 | 10 ml |
| Distilled water | 1000 ml |
| pH 6.8 with NaOH | |

This inoculated flask is incubated for 24 hours at 28° C. on a 220 rpm shaker (2 inch throw) for 24 hours. Eight more unbaffled 250 ml Erlenmeyer flasks (No. 2 seed flask) each containing 40 ml of medium C are then each inoculated with 2 ml per flask of the growth from seed flask No. 1. These eight No. 2 seed flasks are incubated for 24 hours at 28° C. on a 220 rpm shaker (2 inch throw). Twenty, two liter unbaffled Erlenmeyer flasks, containing 500 ml of medium B are then each inoculated with 14 ml per flask of the combined growth of the eight No. 2 seed flasks. These twenty flasks are incubated at 28°, without agitation for 11 days. After 11 days incubation, the contents of these twenty flasks are pooled.

B. Extraction 10.2 liters of whole broth, pH 6.0 was blended in a Waring blender to break up the heavy mycelial pads, centrifuged and the clear supernatant decanted. After filtration the 10 liters of filtrate was extracted with 3 liters of ethyl acetate, yielding 1820 ml of clear extract. A second extraction with 3 liters of ethyl acetate yielded 3350 ml of clear extract. The broth solids were extracted by stirring one hour with 2 liters of methanol and filtering to yield 2100 ml of filtrate.

Aliquots of these extracts were dried and sent for assay by the procedure of Example 1(C), with the following results:

| Volume (ml) | Extract Total Solids (mg) | Total Units of Activity |
|---|---|---|
| 1820 | 1133 | 1,496,695 |
| 3350 | 787 | 314,900 |
| 2100 | 13.15 | 1,144,067 |

C. Gel Filtration

The total solids obtained from the first two extracts in Example 2 (B) were combined, dissolved in methanol and filtered to remove insoluble solids. The 30 ml of filtrate was loaded onto a gel filtration column (2.5 cm×200 cm, 980 ml) packed with Sephadex LH-20 and the sample fractionated according to molecular size using methanol as solvent. With refractive index and U.V. recordings as guides, the best fractions were identified by bioassay.

| Total Solids (mg) | Total Units of Activity |
|---|---|
| Fraction 1 - 89 | 106,271 |
| Fraction 2 - 278 | 1,099,680 |
| Fraction 3 - 779 | 210,357 |

D. Separation and Purification

A sample from Fraction 2 above was prefiltered through a 1-gram bed of Waters Bondapak C18/Porasil B and eluted with five volumes of methanol. The methanol eluate was concentrated to 0.5 ml. This sample was chromatographed, over several runs, on a Waters μC18 column (3.9 mm×30 cm) with methanol: 0.05 M ammonium phosphate, pH 2.9 (75:25), as the developing solvent. Fractions were scanned on a Beckman Spectrophotometer, and those showing absorption maxima at 236 nm, with shoulders at 229 nm and 245 nm were combined and concentrated under reduced pressure to an aqueous solution. The pH of the concentrate was adjusted to 6.5 with 2 M potassium hydroxide and the active components were extracted with ethyl acetate. The organic layer was dried, concentrated to dryness, and the residue was dissolved in 0.3 ml methanol. The methanol solution was chromatographed as above and recycled. Cuts containing earlier eluting component were combined, concentrated to an aqueous solution and extracted with chloroform. The chloroform residue was taken up in methanol and the solvent evaporated under nitrogen. 3.5 mg. of dried product was obtained and identified as hydroxy acid (compound II). Cuts containing the second component were combined and extracted with chloroform as above. 0.87 Mg of dried product was obtained and identified as lactone, (compound I).

EXAMPLE 3

Best Mode of Fermentation of MF-4833 to Produce Compounds I and II

A tube of lyophilized culture of an Aspergillus sp. MF-4833 is opened aseptically and the contents suspended in an unbaffled 250 ml Erlenmeyer flask (seed flask) containing 40 ml of medium C. The inoculated flask is incubated for 48 hours at 28° C. on a 220 rpm shaker (2 inch throw). Two, 250 ml unbaffled Erlenmeyer flasks each containing 40 ml of medium D are then each inoculated with 2 ml per flask of the growth from the seed flask. Medium D has the following composition:

| Medium D | |
|---|---|
| Lactose | 20 g |
| Distillers solubles | 15 g |
| Autolyzed yeast | 5 g |
| Distilled water | 1000 ml |
| ph 7.0 with NaOH | |

These two inoculated flasks are incubated for 96 hours at 28° on a 150 rpm shaker (2 inch throw). After 96 hours incubation the contents of these two flasks is submitted for extraction by the procedure described in Example 2(B). Total production in these flasks is 1450–2000 units/ml.

EXAMPLE 4

Preparation of Compounds I and II

A tube of lyophilized culture of an Aspergillus, MF 4845, is opened aseptically and the contents suspended in an unbaffled 250 ml Erlenmeyer flask (seed flask No. 1) containing 40 ml of medium C. The inoculated flask is incubated for 24–48 hours at 28° C. on a 220 rpm shaker (2 inch throw). A portion (approx. 0.5 ml) of this flask is then used to inoculate a slant tube containing medium E. Medium E. has the following composition:

| Medium E | |
|---|---|
| Yeast Extract | 4 g |
| Malt Extract | 10 g |
| Dextrose | 4 g |
| Agar | 20 g |
| Distilled Water | 1000 ml |
| pH 7.0 with NaOH | |

The inoculated slant tube is incubated for 11 days at room temperature. It is then stored at −60° C. for 3–4 months. A portion of the contents of this slant is then suspended in an unbaffled, 250 ml Erlenmeyer flask (No. 2 seed flask) containing 40 ml of medium C. The inoculated flask is incubated for 24 hours at 28° C. on a 220 rpm shaker (2 inch throw). Six unbaffled 250 ml Erlenmeyer flasks (No. 3 seed flasks) containing 40 ml of medium C are then each inoculated with 2 ml per flask of the growth from the No. 2 seed flask. These six inoculated flasks are incubated for 48 hours at 28° C. on a 220 rpm shaker (2 inch throw). Six unbaffled two liter Erlenmeyer flasks containing 500 ml of medium F are each then inoculated with the contents of No. 3 seed flask. Medium F has the following composition:

| Medium F | |
|---|---|
| Corn steep liquor | 15 g |
| CPC Starch | 20 g |
| Corn meal | 1 g |
| Soybean meal | 4 g |
| Glucose | 5 g |
| Soybean oil | 2.5 g |
| (NH4)2SO4 | 4 g |
| KH2PO4 | 0.3 g |
| CaCo3 | 6 g |
| Distilled Water | 1000 ml |
| pH 6.7 with NaOH | |

The inoculated flasks are incubated for 11 days without agitation at 28° C. After 11 days broth is delivered for extraction by the procedure of Example 2(B). Total production in these flasks is 1231 units/ml.

EXAMPLE 5

Best Mode of Fermentation with MF-4845 to Produce Compounds I and II

A tube of lyophilized culture of an Aspergillus, MF-4845, is opened aseptically and the contents suspended in an unbaffled 250 ml Erlenmeyer flask (seed flask) containing 40 ml of medium C. The inoculated flask is incubated for 30 hours at 28° on a 220 rpm shaker (2 inch throw). An unbaffled, 250 ml Erlenmeyer flask containing 40 ml of medium G is inoculated with 2 ml per flask of the growth from the seed flask. Medium G has the following composition:

| Medium G | |
|---|---|
| Dextrose | 45 g |
| Peptonized milk | 24 g |
| Autolyzed yeast | 2.5 g |
| Polyglycol P2000 | 2.5 ml |
| Distilled water | 1000 ml |
| pH 7.0 with NaOH | |

This inoculated flask is incubated for 120 hours at 28° C. on a 220 rpm shaker (2 inch throw). After 120 hours incubation, the contents of the flask is submitted for extraction by the procedure of Example 2 (B). Total production in this flask is 21,500 units/ml.

EXAMPLE 6

A. Large Scale Fermentation with MF-4833 to Produce Compounds I and II

The medium used in each step of the fermentation comprised:

| Corn steep liquor | 5 g |
|---|---|
| Tomato paste | 40 g |
| Oat Flour | 10 g |
| Glucose | 10 g |
| Trace element solution | 10 ml |
| Distilled water | 1000 ml |
| adjusted to pH 6.8 with sodium hydroxide. | |

The trace element solution comprised:

| FeSO4.7H2O | 1 g |
|---|---|
| MnSO4.4H2O | 1 g |
| CuCl2.2H2O | 25 mg |
| CaCl2 | 100 mg |
| H3BO3 | 56 mg |
| (NH4)6 Mo7O24.4H2O | 19 mg |
| Zn SO4.7H2O | 200 mg |
| distilled water | 1 liter |

All media were checked for sterility before innoculation with a microorganism.

To a 250 ml non-baffled Erlenmeyer flask was charged 40 ml of medium and the contents of one tube of lyophillized organism MF 4833. It was then shaken for 24 hours at 28° C. on a rotary shaker at 220 rpm. New flasks were then charged with 40 ml of medium and 1 ml of the first flask's contents and were shaken an additional 24 hours at 28° C. A 2 liter flask was then charged with 400 ml of medium and 10 ml of the second stage fermentation mixture and this too was shaken for 24 hours at 28° C.

A 200 gallon stainless steel fermentation vat was then charged with 501 liters of a medium comprising:

| | |
|---|---|
| lactose | 2% wt/vol |
| distiller solubles | 1.5% wt/vol |
| autolyzed yeast | 0.5% wt/vol |
| Polyglycol P2000 | 0.25% wt/vol | whose pH was adjusted to 7.0. This was sterilized 15 minutes at 121° C. One liter of the third stage above was then charged and the mixture was incubated at 130 rpm at 28° C. for 96 hours with an air flow of 10 cfm.

B. Isolation of Compound I

About 37.5 lbs. (¾ bag) of a silicaceous filter aid was added to 110 gal. whole broth from the culture of MF-4833 described above and the mixture was filtered through an 18-inch filter press. The clarified filtrate, (pH 6.6) was adjusted to pH 4.0 by careful addition of 450 ml of concentrated hydrochloric acid, and extracted by agitation with about one-third volume (36 gal.) of ethyl acetate. After separation, the upper solvent layer was removed, and the water phase again extracted with ethyl acetate (38 gal.) in a similar fashion. After separation, the two extracts were combined and back-washed by agitation with about twelve gallons of water. After separation, the ethyl acetate solution was concentrated under vacuum at a temperature below 30° C., first in a stirred kettle, and finally in a rotary vacuum evaporator to a residual volume of slightly less than one gallon.

Approximately 1 gal. (3800 ml) of ethyl acetate concentrate from the preceding extraction was further concentrated in a rotary evaporator (ca 10 mm, 40° C. bath) to a syrup and was then concentrated twice more, after addition of about one liter of methylene chloride in two portions, to free the syrup of polar solvent. The final oil of about 300 ml which contained about 250 g of solids by dry weight determination, was made up to about 750 ml with ethyl acetate methylene chloride (30/70; v/v) and 200 g of silica gel was added and mixed in to form a slurry. This was layered over the top of a 14 cm by 36 cm column bed holding 2.5 kg of the same silica gel, in about 7.5 l volume, which had been packed as a slurry in the same solvent mixture. Development with the same solvent was continued until 3 liters of effluent was taken off as forerun.

Development with ethyl acetate-methylene chloride (50/50; v/v) was begun, taking 800 ml effluent fractions. Twelve fractions were taken, then 100% ethyl acetate elution was begun, and after seven more fractions, 100% acetone elution was begun. Fractions four through twenty-four were assayed for bio-activity in the HMG-CoA Reductase inhibition assay referred to in Example 1. Substantial activity was found in fractions 7 through 11. Peak activity was found in fraction 8. It was concentrated to an oil for further purification; dry wt. by solids determination was 9.0 gm.

Fraction 8 from the silica gel column was triturated with 50 ml methylene chloride and filtered; the dried filter cake weighed 4.9 gm. The filtrate was charged to a 2-inch I.D. by 1-meter long column filled with Sephadex LH-20 dextran gel (Pharmacia) swollen and equilibrated in methylene chloride, and the column was eluted with methylene chloride at a rate of 15 ml/min. Compound I was eluted between 0.64 and 0.81 column volumes. Solvent was removed from this peak leaving a slightly brown residue weighing approximately 0.290 gm. This residue (213 mg) was taken up in 1.5 ml of $CH_2Cl_2$—$CH_3CN$ (65-35), charged to a prepacked and equilibrated silica gel column (EM LOBAR Size B) and eluted with $CH_2Cl_2$—$CH_3CN$ (65-35) at 5 ml/min. Evaporation of solvent from the peak eluting between 235 and 360 ml of eluant left 121 mg of crystalline product, m.p. 155°–160° C. HPLC of this material on a EM RP 18 reverse-phase analytical column (E. Merck HIBAR II, Cat. No. 906046) using 0.05 M sodium phosphate pH 3.0-acetonitrile 45-55 as eluant at 2 ml/min. showed a characteristic uv absorbing peak at 11 min.

Eighty-two mg of this material was recrystallized from 0.6 ml of absolute ethanol, then again from 0.4 ml of the same solvent to afford, after drying over-night in a desiccator over $P_2O_5$, 40 mg of white feathery crystals. Analytical HPLC on the system described above gave a single sharp peak at 11 minutes elution time. After further recrystallizations, a melting point of 170°–171° C. was obtained.

The product was identified by spectra, etc., as Compound I. This material, in the in vitro HMG-CoA reductase test (of Example 1) gave an $IC_{50}$ of 0.01 micrograms per milliliter.

EXAMPLE 7

Preparation of Compounds I and II

A. Fermentation

A tube of lyophilized culture MF-4845 is opened aseptically and the contents suspended in an unbaffled 250 ml Erlenmeyer flask (seed flask) containing approximately 10 ml of the Medium which has the following composition:

| Medium | |
|---|---|
| Corn steep liquor | 5 g |
| Tomato paste | 40 g |
| Oatmeal | 10 g |
| Glucose | 10 g |
| Trace Element Solution | 10 ml |
| Distilled water | 1000 ml |
| pH 6.8 with NaOH | |
| Trace Element Solution: | |
| $FeSO_4.7H_2O$ | 1000 mg |
| $MnSO_4.4H_2O$ | 1000 mg |
| $CuCl_2.2H_2O$ | 25 mg |
| $CaCl_2.2H_2O$ | 100 mg |
| $H_3BO_3$ | 56 mg |
| $(NH_4)_6Mo_7O_{24}.4H_2O$ | 19 mg |
| $ZnSO_4.7H_2O$ | 200 mg |
| Distilled Deionized Water | 1000 mg |

The inoculated flask is incubated for 24 hours at 28° C. on a 220 rpm shaker (2 inch throw). An unbaffled 2 liter Erlenmeyer flask containing 500 ml of the medium and then inoculated with 10 ml of the first stage fermentation growth from the seed mixture. This too was shaken 24 hours at 28° C.

A 200 gallon stainless steel fermentation vat was then charged with 485 liters of a medium comprising:

| | |
|---|---|
| Cerelose | 4.5% wt/vol |
| Peptonized milk | 2.5% wt/vol |
| Autolyzed yeast | 0.25% wt/vol |
| Polyglycol P2000 | 0.25% vol/vol | whose pH was adjusted to 7.0. This was sterilized 15 minutes at 121° C. One liter of the second stage above was then charged and the mixture was incubated at 85 rpm for 12 hours then 130 rpm for 84 hours at 28° C. with an air flow of 5 cfm for 12 hours then 10 cfm for 84 hours.

B. Direct Isolation of the Ammonium Salt of Compound II

The broth from the fermentation as in Example 7A (100 gal) is acidified with $H_3PO_4$ to pH of 5. Ethyl acetate (70 gal) is added and the mixture is stirred vigorously. It is then filtered from the mycelia residue and the cake is washed with a small amount of ethyl acetate which is combined with the main extract. The organic phase is separated and mixed with 5 gallons of 0.2 N sodium hydroxide solution. The mixture is stirred vigorously and then allowed to settle. The aqueous layer is separated and the pH is adjusted from 9 to 5 by addition of $H_3PO_4$. It is then extracted, first with 2 gallons of hexane-ethyl acetate 2:1 mixture and then with one gallon of the same mixture. The separate organic extracts are combined and dried over anhydrous $MgSO_4$. The drying agent is then separated by filtration and the cake washed with one liter of the same hexane-ethyl acetate solution, the rinse being combined with the filtrate. This filtrate solution, after further dilution with 2 L of acetone, is stirred while ammonia gas is passed in. The gas is absorbed and a crystalline precipitate appears. When ammonia is no longer absorbed, and a darkening in color is observed in the precipitate, the introduction of ammonia is terminated and the mixture is allowed to stand several hours after which it is filtered. The crude ammonium salt filter cake is washed with acetone to a colorless wash and is then air dried (128 g).

The crude ammonium salt can be recrystallized by dissolving it in a mixture of chloroform, methanol and concentrated aqueous ammonium hydroxide (80:20:2) and filtering the colored insoluble material (about 10% of the crude). The filtrate solution is then diluted with an equal volume of ether. The crystalline, tan colored ammonium salt is obtained by filtration.

Alternatively, the 128 g of crude ammonium salt are suspended in 2 liters toluene and heated to reflux under a water separator while a slow stream of nitrogen is passed through the solution. After about 2½ hours no more water is separated and the effluent gas contains no more ammonia. The hot solution of the lactone is filtered from about 10 g of undissolved, dark material with the help of 13 g of activated charcoal and some Super-Cel. The filtrate is allowed to cool and kept at −20° C. overnight. The crystalline product is filtered, washed with cold toluene and low boiling petrolether and air dried (76.6 g). From the combined and concentrated mother liquor and washing solutions a second batch of 17.4 g is obtained.

The product from this and a second similar batch (total 164.4 g) is recrystallized from ethanol yielding 143.4 g of ≧99% pure compound in several batches.

71.5 G of recrystallized lactone is suspended in 200 ml of 1 N NaOH and 200 ml $CH_3OH$ and stirred until all material is dissolved. The solution is filtered, the methanol evaporated under reduced pressure at 30° C. and 200 ml ethylacetate and 200 ml 2 M $H_3PO_4$ added. The aqueous phase is saturated with NaCl and separated. The organic phase is dried over $MgSO_4$ and filtered and diluted to about 1 liter with ethylacetate and some ether (filter washes). One liter of a mixture of chloroform, methanol and concentrated ammonium hydroxide (80:20:2), followed by 1 liter of acetone are then added with stirring. The precipitated product is filtered and washed with acetone and low boiling petrolether and air dried (75.0 g). A second batch of 2.5 g is obtained from the combined mother liquor and washing solution.

The final purification is achieved by dissolving 75 g of this ammonium salt in 2 liters of hot isopropanol containing 5% concentrated aqueous ammonium hydroxide. The hot solution is rapidly filtered into a preheated flask and allowed to cool to room temperature after the excess of ammonia, which had been lost in the vacuum filtration, is replenished by some $NH_3$ gas. Crystallization is completed by further cooling, first to 0° C. and overnight to −20° C. The product is filtered and washed with isopropanol and acetone at −20° C. and with low boiling petrolether and air dried under exclusion of moisture (65.2 g; ≧99.5% pure).

EXAMPLE 8

Salts of Compound II

To a solution of 40 mg of the product of Example 6 in 2 ml of ethanol is added 1 ml of aqueous NaOH ($10^{-4}$ moles; 1 equivalent). After one hour at room temperature, the mixture is taken to dryness in vacuo to yield the sodium salt of Compound II.

In like manner the potassium salt is prepared using one equivalent of potassium hydroxide.

EXAMPLE 9

L-Lysine Salt of Compound II

A solution of 146 mg of L-lysine in 1.5 ml of 65% ethanol is added to a solution of 440 mg of the ammonium salt of Compound II in 11.5 ml of 85% ethanol. The solvents are distilled off in vacuo. The residue is triturated with 10 ml of warm ethanol, cooled, and filtered, and the white solid is dried to obtain 430 mg of the L-lysine salt of Compound II, m.p. 178°–180° (d).

Anal. Calcd. for $C_{30}H_{52}N_2O_8$: C, 63.35; H, 9.22, N, 4.93; Found: C, 62.80; H, 9.13; N, 4.83.

EXAMPLE 10

L-Arginine Salt of Compound II

In the manner substantially as described in Example 9, a solution of 174 mg of L-arginine base and a solution of 440 mg of the ammonium salt of Compound II are combined. The solvent is evaporated in vacuo, and the residue is triturated with warm ethanol, cooled, filtered, and dried to give the L-arginine salt of Compound II.

EXAMPLE 11

L-Ornithine Salt of Compound II

In the manner substantially as described in Example 9, a solution of 132 mg of L-ornithine free base and a solution of 440 mg of ammonium salt of Compound II are combined. The solvent is evaporated in vacuo and the residue is triturated with warm ethanol, cooled, filtered, and dried to give the L-ornithine salt of Compound II.

EXAMPLE 12

N-Methylglucamine Salt of Compound II

In the manner substantially as described in Example 9, a solution of 195 mg of N-methylglucamine in 1.5 ml of water and 440 mg of Compound III ammonium salt in 11.5 ml of 85% ethanol are combined. The solvent is evaporated in vacuo to obtain the N-methylglucamine salt of Compound II.

EXAMPLE 13

Ethylenediamine Salt of Compound II 18 g of Compound I are dissolved in 180 ml of warm isopropanol and treated with 90 ml of 0.5 M aqueous NaOH solution, aged one hour, diluted with 180 ml of water, evaporated in vacuo to remove the isopropanol, and cooled in an ice bath. Slowly, 90 ml of 0.5 M HCl is added and the mixture is extracted with 2×150 ml of ethyl acetate which is backwashed with 100 ml of water, dried over $MgSO_4$. The solvent is removed in vacuo at low temperature and the residue is dissolved in 150 ml of ethanol. 3 Ml of ethylenediamine is added and the solvent is evaporated in vacuo, and the residue triturated with boiling ethyl acetate, cooled, filtered, and recrystallized from 30 ml of isopropanol and dried in vacuo over $P_2O_5$ to obtain 13.1 g of white crystals, m.p. 152°–153.5° C.

Anal. Calcd. for $(C_{24}H_{37}O_6)^-{}_2 \cdot (C_2H_{10}N_2)^{++}$: C, 66.35; H, 9.35; N, 3.09; Found: C, 66.08; H, 9.49; N, 3.01

EXAMPLE 14

Calcium Salt of Compound II 87.9 mg ammonium salt of Compound II are dissolved in 3 ml $H_2O$ with stirring and heating. 7.4 Mg analytical grade $Ca(OH)_2$ are then added and the mixture stirred and heated until no more ammonia evaporates and only a slight turbidity remains which is separated by centrifugation. The colorless, clear supernatant is lyophilized and probes of the dry material set up for crystallization from various solvents and solvent mixtures. The product crystallizes in needles when a hot concentrated solution in dry isopropanol is allowed to cool to room temperature.

EXAMPLE 15

Tetramethylammonium Salt of Compound II

34 Mg Compound I in 1 ml $CH_2Cl_2$ are treated with 0.04 ml 24% tetramethylammonium hydroxide in methanol. The product is precipitated with ether in partially crystalline form, centrifuged and the precipitate first washed with ether and then recrystallized as hexagonal plates from 1 ml isopropanol by the addition of 5 ml ether and about 5 ml low boiling petrol ether. 27 Mg or 65% are obtained.

| 1H Nmr Spectrum of Compound II Tetramethylammonium Salt | |
|---|---|
| (6 mg/0.35 ml at 25° C. in $CDCl_3$ at 300 MHz) | |
| 0.83 t | (3H, J = 6.5) |
| 0.84 d | (3H, J = 7) |
| 1.02 d | (3H, J = 7) |
| 1.05 d | (3H, J = 7) |
| 1.24 m | (~1H); 1.30–1.80 br.m. envelope |
| 1.88 ddd | (1H, J = 2, 8, 15) |
| 1.98 dd | (1H, 3, 15) |
| 2.16 dd | (1H, J = 8.5, 15.5) |
| 2.23 m | (1H, obscured) |
| 2.32 m | (1H, obscured) |
| 2.37 dd | (1H, J = 3, 15.5) |
| 2.40 m | (~1H, obscured) |
| 3.42 s | (12H, MeN+) |
| 3.79 m | (1H, symmetrical multiplet) |
| 4.06 m | (1H, symmetrical multiplet) |
| 5.32 dt | (1H, J ≃ 3) |
| 5.50 br.s | (1H) |
| 5.79 dd | (1H, J = 6,10) |
| 5.98 d | (1H, J = 10) |

Chemical shifts are in ppm downfield of internal TMS coupling constants in brackets are in Hz.
Abbreviations:
s = singlet,
d = doublet,
t = triplet,
m = multiplet

EXAMPLE 16

Ammonium Salt of Compound II

In the manner substantially as described in Example 13, Compound I is converted to the hydroxy acid, Compound II, extracted into ethyl acetate, dried over $MgSO_4$, filtered, and treated with anhydrous ammonia with stirring and cooling to precipitate the ammonium salt.

EXAMPLE 17

Compound II

453 Mg of the ethylenediamine salt of Compound II are dissolved in 6 ml of 80% ethanol, cooled in an ice bath, treated with 1 ml of 1 M HCl, evaporated in vacuo to remove the ethanol, treated with 3 ml more water, extracted into 2×5 ml of ethyl acetate, and backwashed with water, keeping all solutions cold in an ice bath. The extract is dried over $MgSO_4$ and concentrated to dryness in vacuo to obtain the hydroxy acid as a colorless oil.

A $^{13}C$-nmr spectrum in $CDCl_3$ (190 mg/ml) exhibits chemical shifts for the first six carbons of the hydroxy acid moiety as listed in the table. Upon standing, this hydroxy acid slowly reverts to the lactone.

TABLE $^{13}C$—Nmr Spectrum, Ppm Downfield from Tetramethylsilane

| | Hydroxy Acid, Compound II |
|---|---|
| $C_1$ | 174.8 |
| $C_2, C_4$ | 42.4, 41.6 |
| $C_3$ | 68.8 |
| $C_5$ | 72.3 |
| $C_6$ | 34.9 |

The spectrum of the remainder of the molecule is only slightly changed from the cyclized structure.

EXAMPLE 18

Ethyl Ester of Compound II

A suspension of 500 mg (1.24 mmol) of Compound I (MSD-803) in 20 ml of ethanol is stirred at room temperature under a nitrogen atmosphere. A small piece of sodium (Ca. 1 mg) is added. After 15 minutes a second small piece of sodium is added. After a total reaction time of 30 minutes the homogeneous reaction mixture is diluted with ether, washed with water and with saturated brine and dried ($MgSO_4$). Evaporation of the solvent gives a waxy solid. Analysis by HPCL on a Whatman Partasil 10 PAC column (4.6 mm×25 cm) with 10% isopropanol/hexane pumped at 6 ml/min indicated a mixture of ethyl ester and MSD-803 (77:23). This mixture is separated by medium-pressure chromatography on silica gel (230–400 mesh) by elution with 3% ethanol/methylene chloride. The fractions containing the ester are combined and evaporated to give 358 mg (66%) of an off-white solid, m.p. 67° C.

A portion of this material is recrystallized from hexane to give white needles: m.p. 66.5°–68.5°.

Anal. Calc. for $C_{26}H_{42}O_6$: C, 69.30; H, 9.40; Found: C, 69.22; H, 9.58.

In like manner, by the use of equivalent amounts of methanol, propanol, butanol, isobutanol, t-butanol, amyl alcohol, isoamyl alcohol, 2-dimethylaminoethanol, benzyl alcohol, phenethanol, 2-acetamidoethanol and the like, the corresponding esters are obtained.

EXAMPLE 19

Comparison of I and ML-236B as Inhibitors of Sterol Synthesis in Cell Culture

Employing the procedure of Example 1C, purified samples of Compound I and ML-236B were shown to have $IC_{50}$ of 2.2 and 5.6 nM respectively as inhibitors of HMG-CoA reductase.

What is claimed is:
1. The compound:

II or a pharmaceutically acceptable salt or a lower alkyl ester or a substituted lower alkyl ester wherein the substituent is phenyl, dimethylamino, or acetylamino.

2. The pharmaceutically acceptable salts of the compounds of claim 1, wherein the cation is derived from ammonia, ethylenediamine, N-methylglucamine, lysine, arginine or ornithine.

3. The ammonium salt of compound II of claim 1.

4. The ethylenediamine salt of compound II of claim 1.

5. The lower alkyl esters and substituted lower alkyl esters of the compound of claim 1.

6. The ethyl ester of compound II of claim 1.

7. An antihypercholesteremic pharmaceutical composition comprising a pharmaceutical carrier and an effective amount of the compound:

II or a pharmaceutically acceptable salt or a lower alkyl ester or a substituted lower alkyl ester wherein the substituent is phenyl, dimethylamino, or acetylamino.

8. The composition of claim 7 wherein the compound is a pharmaceutically acceptable salt wherein the cation is derived from ammonia, ethylenediamine, N-methylglucamine, lysine, arginine or ornithine.

9. The composition of claim 7 wherein the compound is the ammonium salt of compound II.

10. The composition of claim 7 wherein the compound is the ethylenediamine salt of compound II.

11. The composition of claim 7 wherein the compound is a lower alkyl ester or substituted lower alkyl ester.

12. The composition of claim 7 wherein the compound is the ethyl ester of compound II.

* * * * *